United States Patent [19]

Fields et al.

[11] Patent Number: 5,770,691

[45] Date of Patent: Jun. 23, 1998

[54] DISCRIMINATORY SUBSTRATES FOR MMP HYDROLYSIS

[75] Inventors: Gregg B. Fields, Brooklyn Park, Minn.; Hideaki Nagase, Fairway, Kans.

[73] Assignees: Regents of the University of Minnesota, Minneapolis, Minn.; The University of Kansas Medical Center, Kansas City, Miss.

[21] Appl. No.: 464,337

[22] Filed: Jun. 5, 1995

[51] Int. Cl.[6] .......................... A61K 38/04; A61K 38/00; A61K 7/16; C12Q 1/37

[52] U.S. Cl. .......................... 530/328; 530/300; 435/23; 435/24; 424/49; 424/94.3

[58] Field of Search ........................ 435/23, 24; 530/327, 530/328, 300; 424/49, 94.3

[56] References Cited

PUBLICATIONS

Weingarten et al., "Synthetic Substrates of Vertebrate Collagenase," *Biochemistry*, 24, 6730–6734 (1985). Month not available.

Wilhelm et al., "Matrix Metalloproteinase–3 (Stromelysin–1); Identification as the cartilage acid metalloprotease and effect of pH on catalyic properties and calcium affinity," *J. Biol. Chem.*, 268, 21906–21913 (Oct. 15, 1993).

Wu et al., "Sites of Stromelysin Cleavage in Collagen Types II, IX, X, and XI of Cartilage," *J. Biol. Chem.*, 266, 5625–5628 (Mar. 25, 1991).

Ogata et al., "Matrix Metalloproteinase 3 (Stromelysin) Activates the Precursor for the Human Matrix Metalloproteinase 9," *J. Biol. Chem.*, 267, 3581–3584 (Feb. 25, 1992).

Okada et al., "Immunolocalisation of matrix metalloproteinase 3 (stromelysin) in rheumatoid synovioblasts (B cells): correlation with rheumatoid arthritis," *Annals of the Rheumatic Diseases*, 48, 645–653 (Aug. 1989).

Okada et al., "Matrix metalloproteinase 2 from human rheumatoid synovial fibroblasts; Purification and activation of the precursor and enzymic properties," *Eur. J. Biochem.*, 194, 721–730 (Dec. 27, 1990).

Poe et al., "High Pressure Gel–Permeation Assay for the Proteolysis of Human Aggrecan by Human Stromelysin–1: Kinetic Constants for Aggrecan Hydrolysis," *Arch. Biochem. Biophys.*, 298, 757–759 (Nov. 1, 1992).

Stack et al., "Comparison of Vertebrate Collagenase and Gelatinase Using a New Fluorogenic Substrate Peptide," *J. Biol. Chem.*, 264, 4277–4281 (Mar. 15, 1989).

Stetler–Stevenson et al., "Tumor cell interactions with the extracellular matrix during invasion and metastasis," *Annu. Rev. Cell. Biol.*, 9, 541–573 (1993). Month not available.

Suzuki et al., "Mechanisms of Activation of Tissue Procollagenase by Matrix Metalloproteinase 3 (Stromelysin)," *Biochemistry*, 29, 10261–10270 (1990). Month not available.

Teahan et al., "Substrate Specificity of Human Fibroblast Stromelysin. Hydrolysis of Substance P and its Analogues," *Biochemistry*, 28, 8497–8501 (1989). Month not available.

(List continued on next page.)

*Primary Examiner*—Louise Leary
*Attorney, Agent, or Firm*—Mufting, Raasch & Gebhardt, P.A.

[57] ABSTRACT

A method of screening a sample for the presence of a matrix metalloproteinase employing discriminatory peptide substrates is provided. The method involves providing a peptide substrate of 6–14 amino acid residues containing at least one matrix metalloproteinase cleavage site. The peptide substrate contains Mca as a fluorogenic group and Lys(Dnp) as a quenching group separated by at least four amino acid residues, wherein the peptide substrate is specific for the matrix metalloproteinase of interest. The peptide substrate is combined with a sample containing at least one matrix metalloproteinase to form a mixture. The fluorescence of the mixture is monitored to determine if the matrix metalloproteinase of interest is present.

2 Claims, 2 Drawing Sheets

PUBLICATIONS

Weingarten et al., "Cleavage site specificity of vertebrate collagenases," *Biochem. Biophys. Res. Commun.*, 139, 1184–1187 (Sep. 30, 1986).

Mast et al., "Kinetics and Physiologic Relevance of the Inactivation of $\alpha_1$–Proteinase Inhibitor,$\alpha_1$–Antichymotrypsin, and Antithrombin III by Matrix Metalloproteinases–1 (Tissue Collagenase), –2 (72–kDa Gelatinase/Type IV Collagenase), and –3 (Stromelysin)," *J. Biol. Chem.*, 266, 15810–15816 (Aug. 25, 1991).

Morodomi et al., "Purification and characterization of matrix metalloproteinase 9 from U937 monocytic leukaemia and HT1080 fibrosarcoma cells," *Biochem. J.*, 285, 603–611 (Jul. 15, 1992).

Nagase et al., "Design and Characterization of a Fluorogenic Substrate Selectively Hydrolyzed by Stromelysin 1 (Matrix Metalloproteinase–3)," *J. Biol. Chem.*, 269, 20952–20957 (Aug. 19, 1994).

Nagase et al., "Stepwise Activation Mechanisms of the Precursor of Matrix Metalloproteinase 3 (Stromelysin) by Proteinases and (4–Aminophenyl)mercuric Acetate," *Biochemistry*, 29, 5783–5789 (1990). Month not available.

Netzel–Arnett et al., "Comparative Sequence Specifities of Human 72– and 92–kDa Gelatinases (Type IV Collagenases) and PUMP (Matrilysin)," *Biochemistry*, 32, 6427–6432 (1993). Month not available.

Netzel–Arnett et al., "Continuously Recording Fluorescent Assays Optimized for Five Human Matrix Metalloproteinases," *Anal. Biochem.*, 195, 86–92 (1991). Month not available.

Netzel–Arnett et al., "Sequence Specifities of Human Fibroblast and Neutrophil Collagenases," *J. Biol. Chem*, 266, 6747–6755 (Apr. 15, 1991).

Niedzwiecki et al., "Substrate Specificity of the Human Matrix Metalloproteinase Stromelysin and the Development of Continuous Fluorometric Assays," *Biochemistry*, 31, 12618–12623 (1992). Month not available.

Fields, G.B. et al., "Principles and Practice of Solid–Phase Peptide Synthesis," *Synthetic Peptides: A User's Guide*, G.A. Grants, Ed.; W.H. Freeman: New York; pp. 77–183 (1992).

Fields, G.B. et al., "Sequence Specificity of Human Skin Fibroblast Collagenase; Evidence for the Role of Collagen Structure in Determining the Collagenase Cleavage Site," *J. Biol. Chem.*, 262, 6221–6226 (May 5, 1987).

Flannery et al., "Identification of a Stromelysin Cleavage Site within the Interglobular Domain of Human Aggrecan," *J. Biol. Chem.*, 267, 1008–1014 (Jan. 15, 1992).

Geoghegan et al., "Site–Directed Double Fluorescent Tagging of Human Renin and Collagenase (MMP–1) Substrate Peptides Using the Periodate Oxidation of N–Terminal Serine. An Apparently General Strategy for Provision of Energy–Transfer Substrates for Proteases," *Bioconjugate Chem.*, 4, 537–544 (1993). Month not available.

Ito et al., "Evidence that Human Rheumatoid Synovial Matrix Metalloproteinase 3 is an Endogenous Activator of Procollagenase," *Archives of Biochem. Biophys.*, 267, 211–216 (Nov. 15, 1988).

King et al., "A cleavage method which minimizes side reactions following Fmoc solid phase peptide synthesis," *Int. J. Peptide Protein Res.*, 36, 255–266 (Sep. 1990).

Knäuper et al., "Direct activation of human neutrophil procollagenase by recombinant stromelysin," *Biochem. J.*, 295, 581–586 (Oct. 15, 1993).

Knight et al., "A novel coumarin–labelled peptide for sensitive continuous assays of the matrix metalloproteinases," *FEBS Lett.*, 296, 263–266 (Jan. 1992).

Azzo et al., "Purification and Characterization of an Acid Metalloprotease from Human Articular Cartilage," *J. Biol. Chem.*, 261, 5434–5441 (Apr. 25, 1986).

Berman et al., "Rapid Optimization of Enzyme Substrates Using Defined Substrate Mixtures," *J. Biol. Chem.*, 267, 1434–1437 (Jan. 25, 1992).

Bickett et al., "A High Throughput Fluorogenic Substrate for Interstitial Collagenase (MMP–1) and Gelatinase (MMP–9)," *Anal. Biochem.*, 212, 58–64 (1993). Month not available.

Enghild et al., "Interaction of Human Rheumatoid Synovial Collagenase (Matrix Metalloproteinase 1) and Stromelysin (Matrix Metalloproteinase 3) with Human $\alpha_2$–Macroglobulin and Chicken Ovostatin," *J. Biol. Chem.*, 264, 8779–8785 (May 25, 1989).

Fields, C.G. et al., "The Development of High–Performance Liquid Chromatographic Analysis of Allyl and Allyloxycarbonyl Side–Chain–Protected Phenylthiohydantoin Amino Acids," *Anal. Biochem.*, 203, 245–251 (1992). Month not available.

Fields, C.G. et al., "Edman Degradation Sequence Analysis of Resin–Bound Peptides Synthesized by 9–Fluorenylmethoxycarbonyl Chemistry," *Peptide Res.*, 6, 39–46 (1993). Month not available.

Fields, C.G. et al., "HBTU Activation for Automated Fmoc Solid–Phase Peptide Synthesis," *Peptide Res.*, 4, 95–101 (1991). Month not available.

Fields, G.B., "The Application of Solid Phase Peptide Synthesis to the Study of Structure Function Relationships in the Collagen–Collagenase System," Ph.D. Thesis; Florida State University, Tallahassee, FL; pp. 136–176 (1988). Month not available.

Fields, G.B., "A Model for Interstitial Collagen by Mammalian Collegenases," *J. theor. Biol.*, 153, 585–602 (1991). Month not available.

C. G. Fields et al., "Edman degradation sequence analysis of resin–bound peptides: Characterization of unusual and side chain protected PTH–amino acids," in *Peptides 1992;* C. H. Schneider et al., Eds.; ESCOM: Leiden, The Netherlands; pp. 447–448 (1992). Month not available.

Nagase et al., "Substrate specificities and activation mechanisms of matrix metalloproteinases," *Biochem. Soc. Trans.* (U.K.), 19(3), 715–718 (1991). Month not available.

DISCRIMINATORY SUBSTRATES FOR MMP HYDROLYSIS

STATEMENT OF GOVERNMENT RIGHTS

The present invention was made with the support of the United States Government via grants from the National Institutes of Health (Grants AR 39189, AR 40994, KD 44494, and AR 01929). The government has certain rights in the invention.

BACKGROUND OF THE INVENTION

Matrix metalloproteinases (MMPs) are a family of tissue collagenases that play a role in the normal turnover of the extracellular matrix. MMPs share common properties such as an active center containing zinc, a requirement for calcium ions for enzymatic stability, activation of zymogen forms by organomercurials, inhibition by tissue collagenase inhibitors that inhibit only MMPs, and sequence homology to collagenase. There are four categories of MMPs in humans. These include fibroblast and neutrophil interstitial collagenases, gelatinases, stromelysins, and matrilysin.

The MMP family has been implicated in a variety of disease states, including arthritis, periodontal disease, and tumor cell invasion and metastasis. Studies with tumorigenic cells have reported correlations between expression of interstitial collagenase (MMP-1), gelatinase A (MMP-2), stromelysin 1 (MMP-3), matrilysin (MMP-7), gelatinase B (MMP-9) and/or stromelysin 3 (MMP-11) and invasive and metastatic behaviors. It is not clear, however, which MMPs are of primary importance for tumor cell invasion, or if invasive behavior can be assigned to a single member of the MMP family. Such information would be extremely valuable for the development of diagnostic assays, therapeutics, or preventative regimens.

Synthetic peptide-based assays can be developed to discriminate between specific enzymes and/or enzyme types. A peptide substrate is a molecule upon which an enzyme promotes a chemical change. The use of synthetic peptides as substrates for an enzyme such as an MMP is advantageous because the number of variables can be easily controlled, synthetic peptides have less of a tendency to aggregate than native proteins at the concentrations employed in these assays, and contamination with metals or other compounds is reduced or eliminated. One additional advantage of using synthetic peptides as a substrate in an assay to discriminate between enzymes and/or enzyme types is that moieties required for assay monitoring, such as chromophores or fluorophores, can be incorporated easily.

Fluorogenic substrates provide a particularly convenient enzyme assay method. They can be monitored continuously and utilized at reasonably low concentrations. In these assays, a peptide substrate containing an MMP cleavage site flanked on one side by a fluorogenic group and on the other side by a quenching group that masks the fluorescence of the fluorogenic group when the two groups are in close proximity, is incubated with an MMP. When the peptide is cleaved by the MMP, the fluorogenic group is no longer in close proximity to the quenching group and thus no longer masked by the quenching group. The change in the fluorescence in the mixture is monitored over time. However, fluorogenic amino acid residues in the MMP can interfere with the sensitivity of the assay at the wavelengths employed in the fluorescence-based assay.

While synthetic fluorogenic substrates for identifying a subset of MMPs have been described, none of these substrates is hydrolyzed by a unique MMP. For example, the Mca-Pro-Leu-Gly-Leu-Dpa-Ala-Arg substrate and the Dnp-Pro-Leu-Gly-Leu-Trp-Ala-D-Arg-NH$_2$ substrate are hydrolyzed by MMP-1, MMP-2, MMP-3, and MMP-7, while the Dnp-Pro-Cha-Gly-Cys(CH$_3$)-His-Ala-Lys(Nma)-NH$_2$, substrate is hydrolyzed by at least MMP-1 and MMP-9. See Fields, *The Application of Solid Phase Peptide Synthesis to the Study of Structure-Function Relationships in the Collagen-Collagenase System*, Ph.D. Thesis, Florida State University, Tallahassee, Fla., pp. 136–176, (1988); Stack et al., *J. Biol. Chem.*, 264, 4277 (1989); Knight et al., *FEBS Lett.*, 296, 263 (1992); and Bickett et al., *Anal. Biochem.*, 212, 5 (1993).

Thus, what is needed are fluorogenic substrates which can discriminate between different MMPs and can be monitored without interference from amino acid residues present in the MMP.

SUMMARY OF THE INVENTION

The present invention provides a method of screening a sample for the presence of an MMP. The present method comprises providing a peptide substrate of six to fourteen amino acid residues containing at least one MMP cleavage site. The peptide substrate is specific for the matrix metalloproteinase of interest and contains Mca as a fluorogenic group and Lys(Dnp) as a quenching group. The fluorogenic and quenching groups are separated by at least four amino acid residues. The peptide substrate is mixed with a sample containing at least one MMP to form a mixture. The fluorescence of the mixture is measured to determine if the MMP of interest is present.

A preferred embodiment of the method of the invention includes the use of a peptide substrate wherein the fluorogenic and quenching groups are separated by no more than twelve amino acid residues. That is, they have no more than twelve amino acid residues between them. Preferred embodiments of the method of the invention include the use of the peptides Mca-Arg-Pro-Lys-Pro-Tyr-Ala-Nva-Trp-Met-Lys(Dnp)-NH$_2$ and Mca-Arg-Pro-Lys-Pro-Val-Glu-Nva-Trp-Arg-Lys(Dnp)-NH$_2$. Another preferred embodiment of the method of the invention is when at least one MMP being detected is an enzymatically active MMP. Another preferred embodiment of the method of the invention is when the MMP is MMP-3.

Another embodiment of the invention is a method of screening a sample for the presence of MMP-9 comprising providing the MMP-9 specific peptide substrate Arg-Pro-Lys-Pro-Tyr-Ala-Nva-Trp-Met wherein a fluorogenic group is present on the amino terminus of the peptide substrate and a quenching group is present on the carboxy terminus of the peptide substrate. The peptide substrate is mixed with a sample containing at least one MMP to form a mixture, and the fluorescence of the mixture is monitored for a period of time to determine if MMP-9 is present. A preferred embodiment of the invention is when at least one MMP is in an enzymatically active state. A more preferred embodiment of the invention is when the enzymatically active MMP is MMP-9. and the fluorescence of the mixture is monitored for a period of time to determine if MMP-9 is present. A preferred embodiment of the invention is when at least one MMP is in an enzymatically active state. A more preferred embodiment of the invention is when the enzymatically active MMP is MMP-9.

Another embodiment of the invention is a method of screening a sample for the presence of MMP-3 comprising providing the MMP-3 specific peptide substrate Arg-Pro-Lys-Pro-Val-Glu-Nva-Trp-Arg wherein a fluorogenic group is present on the amino terminus of the peptide substrate and a quenching group is present on the carboxy terminus of the peptide substrate. The peptide substrate is mixed with a sample containing at least one MMP to form a mixture and the fluorescence of the mixture is monitored to determine if MMP-3 is present. A preferred embodiment of the invention is when at least one MMP is in an enzymatically active state. A more preferred embodiment of the invention is when the enzymatically active MMP is MMP-3.

The present invention also provides a peptide compound which is a discriminatory substrate for MMP-3. This substrate is Mca-Arg-Pro-Lys-Pro-Val-Glu-Nva-Trp-Arg-Lys (Dnp)-NH$_2$. The present invention also provides a peptide compound which is a specific substrate for MMP-9. This substrate is Mca-Arg-Pro-Lys-Pro-Tyr-Ala-Nva-Trp-Met-Lys(Dnp)-NH$_2$.

As used herein, a "matrix metalloproteinase" means an enzyme with extracellular matrix degrading activity. The term "discriminatory substrate" means a peptide that is preferentially and rapidly cleaved by only one matrix metalloproteinase. "Preferential and rapid cleavage" means a ten-fold more rapid hydrolysis ($k_{cat}/K_M$) by one matrix metalloproteinase versus all others. The term "specific" in reference to a peptide substrate means that the peptide substrate is cleaved by a particular MMP.

As used herein, the term "fluorogenic" group means any chemical moiety that can be incorporated into a peptide such that the presence of the chemical moiety in the peptide is detectable by the fluorescence of the moiety when the peptide containing the moiety is exposed to a particular wavelength of light. A preferred set of parameters to detect the fluorogenic group is $\lambda_{ex}$=325 nm and $\lambda_{em}$=393 nm.

As used herein, a "quenching group" is a chemical moiety that can be incorporated into a peptide such that the presence of the quenching group masks or quenches the signal emitted by a fluorogenic group when the fluorogenic group is exposed to a particular wavelength of light. In order to quench the signal of the fluorogenic group, the quenching group is in close proximity to the fluorogenic group. "Close proximity" means that the fluorogenic and quenching groups are separated by no more than twelve amino acid residues within the same peptide molecule. That is, no more than twelve amino acid residues are between these groups.

As used herein, an "enzymatically active state" in reference to an MMP means a state wherein an MMP, in the presence of all co-factors necessary for MMP activity (e.g., calcium), is capable of cleaving a peptide substrate having a cleavage site that is specific for that particular MMP. Generally this state is achieved by the proteolytic cleavage of the zymogen form of the MMP. In contrast, an "enzymatically inactive state" in reference to an MMP is a state wherein an MMP, in the presence of all necessary co-factors, is incapable of cleaving a peptide substrate having a cleavage site that is specific for that particular MMP. Generally this state is when the MMP is in its zymogen form. A zymogen is an enzymatically inactive form of a protein which is subsequently modified to the active form.

DETAILED DESCRIPTION OF THE INVENTION

Figure 1:
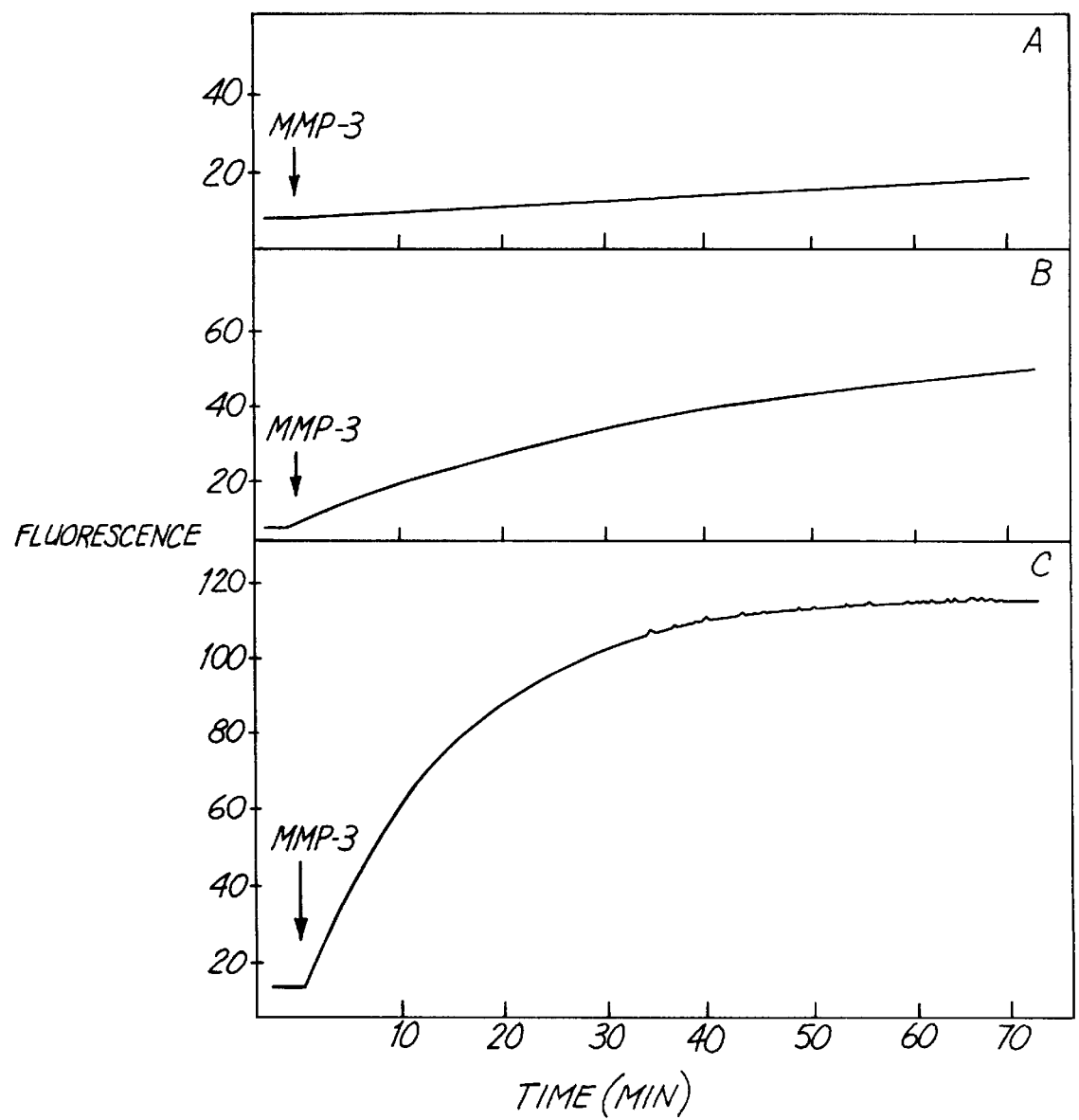
FIG. 1 Continuous fluorometric assay of MMP-3 with (A) Mca-Pro-Lys-Pro-Gln-Gln-Phe-Phe-Gly-Leu-Lys(Dnp)-Gly (NFF-1), (B) McaArg-Pro-Lys-Pro-Tyr-Ala-Nva-Trp-Met-Lys(Dnp)-NH$_2$ (NFF-2), and (C) McaArg-Pro-Lys-Pro-Val-Glu-Nva-Trp-Arg-Lys(Dnp)-NH2 (NFF-3). Assays were performed at 37° C., pH 7.5, by reacting 1 $\mu$M substrate and 200 ng of 45-kDa MMP-3 in a 1 mL solution. Fluorescence was read with $\lambda_{ex}$=325 nm and $\lambda_{em}$=393 nm.

The expression of MMPs has been associated with a variety of diseases. The development of discriminatory substrates may allow for the assignment of a specific MMP activity for pathogenesis. This identification would result in advances in the identification of the pathogenic mechanism (s) and therapeutics for a particular disease.

An MMP peptide substrate that is specifically and rapidly cleaved by one particular MMP is useful for determining if the presence of that MMP is correlated with a particular disease state. Generally, an MMP peptide substrate is synthesized or provided with a known or putative cleavage site for the MMP of interest. The method employed to synthesize the peptide substrate can be any method well known in the art wherein intact fluorogenic and quenching groups can be incorporated into the peptide substrate. See Nagase et al. (*J. Biol. Chem.*, 269, 20952 (1994); Knight et al. (*FEBS Lett.*, 296, 263 (1992); Stack et al. (*J. Biol. Chem.*, 264, 4277 (1989). The fluorogenic and quenching groups are on opposite sides of the cleavage site to provide a convenient way to monitor the cleavage of the peptide substrate. The fluorogenic group is at the amino terminus of the peptide substrate and the quenching group is at the carboxy terminus. The cleavage site is the site between two amino acid residues in a peptide that are joined by a peptide bond prior to exposure to an MMP and, which after exposure to the MMP, are no longer physically linked via that peptide bond. Other amino acid residues that may contribute to the cleavage specificity can also be included in the peptide substrate.

Any fluorogenic group that is more fluorescent than Trp (tryptophan) and where the detection of the change in fluorescence of the mixture of the fluorogenically-labelled peptide substrate incubated with a sample containing at least one MMP is not affected by the fluorescence of the Trp residues in the MMP can be used in the methods and compositions of the present invention. A particularly preferred fluorogenic group useful in the present invention is Mca (7-methyoxycoumarin-4-yl)acetyl). Mca is more fluorescent than Trp. Also, the fluorescence of Trp residues in the MMP will not interfere with detection of the change in fluorescence of the mixture of the Mca-labelled peptide substrate incubated with a sample containing at least one MMP over time.

Quenching groups useful in the present invention include, but are not limited to, Lys(Dnp) (lysine-2,4-dinitrophenyl), Dpa (N-3-(2,4-dinitropnenyl)-L-2,3-diaminopropionyl), and Dnp (2,4-dinitrophenyl). Any quenching group that is capable of masking the fluorescence of the fluorogenic group when the quenching group is in close proximity to the fluorogenic group can be used in the methods and compositions of the present invention. Lys(Dnp) is the preferred quenching group of the present invention.

To determine substrate specificity, a peptide substrate is incubated with a sample containing a set of individual MMPs, or a mixture of MMPs, that are preferably in an enzymatically activated state. MMPs are synthesized as enzymatically inactive precursors known as zymogens. After proteolytic cleavage, an MMP zymogen becomes an enzymatically active MMP. The concentration of the activated form of a purified MMP preparation can be determined by titrating the MMP with a tissue inhibitor specific for that MMP by methods well known in the art.

It is to be understood that the amount of peptide substrate to be incubated with a sample containing an MMP or MMP mixture will vary, depending on the amount of MMP present. In all cases, however, the amount of peptide substrate will be in excess relative to the amount of MMP. For each concentration of peptide substrate analyzed, a range of concentrations of each MMP is tested and the rate of cleavage monitored. The range of MMP concentrations can be provided by varying the volume of a single concentration of a stock solution of an MMP or by adding the same volume of different concentrations of stock solutions of an MMP to the same final volume of reaction mixture. A preferred concentration of peptide substrate is about 2–7.5 $\mu$M. A preferred final concentration of an MMP is about 2–20 nM. Preferred reaction conditions are at temperatures between 20°–40° C. in a pH buffered solution (pH of about 5.0 to 9.0) containing calcium. For example, a 1 $\mu$M solution of a fluorogenically labelled peptide substrate with a putative MMP-3 specific cleavage site is incubated with 200 ng of purified and activated MMP-3 or MMP-1 in a 1 mL solution containing 10 mM calcium chloride and 0.02% sodium azide at pH 7.5 and 37° C. The fluorescence in the mixture is monitored at a wavelength where the fluorescence emitted by Trp residues is not detectable and recorded over a period of about 60 minutes. If the peptide substrate is specific for MMP-3 under these reaction conditions, then only the mixture with MMP-3, rather than one with MMP-1, or any other MMP, will demonstrate a significant increase in fluorescence over time.

Once such a discriminatory peptide substrate is identified, tissue or fluid samples from patients with a particular disease can be screened for the presence of that MMP. For example, the rate of cleavage of a discriminatory substrate incubated with synovial fluid from arthritis patients can be compared to the rate of cleavage of that same substrate with synovial fluid of non-arthritic patients. If the rate of cleavage of the substrate in arthritic patients is significantly greater, then the presence of the MMP which specifically cleaves that substrate is correlated with a particular disease, arthritis. An assay specific for MMP-3 would be especially valuable because MMP-3 has a broad substrate specificity and can participate in the activation of zymogens of MMP-1, MMP-3, and MMP-9. These two properties of MMP-3, that MMP-3 can cleave many different substrates and can activate other MMPs, make MMP-3 a good candidate for an enzyme which is involved in the pathogenesis of a number of connective tissue diseases.

It is to be understood that the sample to be assayed may contain an isolated or pure MMP, or mixtures of a variety of MMPs, of either known or unknown concentration. It may be a biological sample containing an MMP, or a mixture of MMPs, of either known or unknown concentration. Alternatively, the sample being tested may be a sample with no detectable MMP. The amount of MMP in a sample combined with the peptide substrate to form the mixture must be an amount which can cleave a fluorgenically labelled peptide with a quencher group such that the cleavage reaction can be detected by monitoring the change in the level of fluorescence over time.

The invention has been described with reference to various specific and preferred embodiments and will be further described by reference to the following detailed examples. It is understood, however, that there are many extensions, variations, and modifications on the basic theme of the present invention beyond that shown in the examples and description, which are within the spirit and scope of the present invention.

I. EXPERIMENTAL PROCEDURES

Materials

All standard peptide synthesis chemicals were analytical reagent grade or better and purchased from Applied Biosystems, Inc. (Foster City, Calif.) or Fisher Scientific (Pittsburgh, Pa.). 1,8-diazabicyclo[5.4.0]undec-7-ene (DBU), 1,2-ethanedithiol (EDT), and thioanisole were from Aldrich Chemical Co., Inc. (Milwaukee, Wis.), 4-hydroxymethylphenoxy (HMP) copoly(styrene-1%-divinylbenzene resin (substitution level=0.97 mmol/g) from Bachem Biosciences (Philadelphia, Pa.), 9-fluorenylmethoxycarbonyl-4-(2',4'-dimethoxyphenylaminomethyl)phenoxy (Fmoc-DMPAMP) resin (substitution level=0.43 mmol/g) from Novabiochem (La Jolla, Calif.), 2-(1H-benzotriazole-1-yl)-1,1,3,3-tetramethyluronium hexafluorophosphate (HBTU) from Richelieu Biotechnologies (St.-Hyacinthe, Quebec), and Lys (2,4-dinitrophenyl) (Dnp) from Sigma Chemical (St. Louis, Mo.). Fmoc-amino acid derivatives were obtained from Millipore Corporation (Bedford, Mass.) or Novabiochem. Amino acids are of the L-configuration (except for Gly).

Preparation of Fmoc-Lys(Dnp)

Fmoc-Lys(Dnp) was prepared from Lys(Dnp) as follows. Fmoc N-hydroxysuccinimide ester (1.89 g; 5.60 mmol) was dissolved in 30 mL of dimethoxyethane and stored at 4° C. Lys(Dnp) (1.63 g; 4.67 mmol) was dissolved in 10 mL of 10% aqueous $Na_2CO_3$ and added slowly to the dimethoxyethane solution. The reaction proceeded for 2 hours at 4° C. and overnight at room temperature. The solution was filtered, and the filtrate acidified to a pH of about 3 with concentrated HCl. Dimethoxyethane was removed by heating the solution under reduced pressure. The solution was extracted with ethyl acetate, and the ethyl acetate layer reduced by heating under reduced pressure to an oil. The oil [Fmoc-Lys(Dnp)] was used without further purification.

Preparation of Fmoc-Lys(Dnp) Resins

Fmoc-Lys(Dnp)-Gly-HMP resin was prepared as follows. Fmoc-Gly (5.77 g; 19.4 mmol), 1-hydroxybenzotriazole (HOBt) (2.97 g; 19.4 mmol), and 4-(dimethylamino) pyridine (DMAP) (0.237 g; 1.94 mmol) were dissolved in 100 mL dichloromethane-N,N-dimethylformamide (DCM-DMF) (1:1) and added to 5.0 g HMP resin (4.85 mmol). N,N'-diisopropylcarbodiimide (DIPCDI) (3.04 mL; 19.4 mmol) was added, and esterification proceeded for 3 hours. An additional 200 mL of DMF was added, and the reaction continued for 3.5 hours. The resin was washed with DMF and DCM and stored under vacuum overnight. Fulvene-piperidine analysis (G. B. Fields et al., *Synthetic Peptides. A User's Guide* (Grant, G. A., ed.), W. H. Freeman and Co., New York, pp. 77–183 (1992)) gave a substitution level of 0.45 mmol/g for Fmoc-Gly-HMP resin. Fmoc-Gly-HMP resin (3.0 g; 1.36 mmol) was deprotected by treatment with 50 mL DBU-piperidine-DMF (1:1:48) for 0.5 hours and washed 3 times with DMF. Fmoc-Lys(Dnp) (0.232 g; 4.07 mmol) and HOBt (0.623 g; 4.07 mmol) were dissolved in 50 mL in DCM-DMF (1:1) and added to the resin. DIPCDI (0.637 mL; 4.07 mmol) was added and coupling proceeded for 3.5 hours. The resultant FmocLys(Dnp)-Gly-HMP resin was washed with DMF and DCM and stored under vacuum.

Fmoc-Lys(Dnp)-DMPAMP resin was prepared as follows. Fmoc-DMPAMP resin (2.0 g; 0.86 mmol) was deprotected by treatment with 20 mL piperidine-DMF (1:1) for 0.5 hours and washed 3 times with DMF. Fmoc-Lys(Dnp) (0.2 g; 3.5 mmol) and HOBt (0.536 g; 3.5 mmol) were dissolved in 20 mL in DCM-DMF (1:1) and added to the resin. DIPCDI (0.548 mL; 3.5 mmol) was added and coupling proceeded for 4.5 hours. The resultant Fmoc-Lys(Dnp)-DMPAMP resin was washed with DMF and DCM and stored under vacuum.

Peptide Synthesis and Purification

Incorporation of individual amino acids was by Fmoc solid-phase methodology on an Applied Biosystems 431A Peptide Synthesizer using cycles described previously (Fields et al., *Peptide Res.* 4, 95 (1991); C. G. Fields et al., *Anal. Biochem.* 203, 245 (1992)). Peptide-resins were analyzed prior to (7-methoxycoumarin-4-yl)acetyl (Mca) incorporation by Edman degradation analysis to evaluate the efficiency of assembly (Fields and Fields, *Peptides* 1992 (Schneider, C. H. and Eberle, A. N., eds.), Escom, Leiden, The Netherlands, pp. 447–448, 1992; Fields et al., *Peptide Res.* 6, 39 (1993)). The N-termini of peptide-resins were acylated with 7-methoxycoumarin-4-acetic acid using standard synthesis cycles (Fields et al., *Peptide Res.* 4, 95 (1991); Fields et al., *Synthetic Peptides. A User's Guide* (Grant, G. A., ed.), W. H. Freeman and Co., New York, pp. 77–183 (1992)) and 2–4 hour coupling times. Mca-peptides were cleaved from the resin and side-chain deprotected by treatment with trifluoroacetic acid (TFA) plus appropriate scavengers (King et al., *Int. J. Peptide Protein Res.*, 36, 255 (1990). Peptides were purified by preparative reversed-phase high-performance liquid chromatography (RP-HPLC) on a Beckman System Gold with a Regis Chemical ODS $C_{18}$ column (10 μm particle size, 60 Å pore size, 250×21.1 mm). The elution gradient was 20–100% acetonitrile containing 0.1% TFA in 35 minutes at a flow rate of 5.0 mL/minute. Detection was at 235 nmn. Analytical RP-HPLC was performed on a Hewlett-Packard 1090 Liquid Chromatograph equipped with a Dynamax $C_{18}$ column (12 μm particle size, 300 Å pore size, 250×4.6 mm). The elution gradient was 0–100% acetonitrile containing 0.1% TFA in 60 minutes at a flow rate of 1.0 mL/minute. Diode array detection was at 220, 254, and 280 nm.

Peptide Analyses

Ninhydrin analysis as described in G. B. Fields et al., *Synthetic peptides. A User's Guide* (Grant G. A., ed.), W. H. Freeman and Co., New York, pp.77–183 (1992) was used to monitor all manual coupling and deprotection steps. Edman degradation sequence analysis of peptide-resins was performed on an Applied Biosystems 477A Protein Sequencer/120A Analyzer as described previously in Fields et al., *Pept. Res.*, 6, 39 (1993). Fulvene-piperidine concentrations (301 nm) and scanning UV spectra (200–320 nm) were determined with a Beckman DU-70 Spectrophotometer. Peptides were characterized by either electrospray mass spectrometry (ESMS) as described in Fields et al., *Pept. Res.*, 6, 39 (1993) or fast atom bombardment mass spectrometry (FABMS) on a VG 7070E-HF with a glycerol matrix.

Matrix Metalloproteinases

All MMPs were purified in zymogen form. ProMMP-1 (Suzuki et al., *Biochem.*, 29, 10261 (1990)), proMMP-2 (Okada et al., *Eur. J. Biochem.*, 194, 721 (1990)), and proMMP-3 (Ito et al., *Arch. Biochem. Biophys.*, 267, 211 (1988)) were purified from the culture medium of human rheumatoid synovial cells stimulated with rabbit macrophage-conditioned medium. ProMMP-9 was purified from the culture medium of HT-1080 cells as described in Morodomi et al., *Biochem. J.*, 285, 603 (1992). ProMMP-2 and proMMP-9 were activated by reacting with 1 mM 4-aminophenylmercuric acetate at 37° C. for 45 minutes and 32 hours, respectively. ProMMP-1 was activated by reacting with 1 mM 4-aminophenylmercuric acetate and an equimolar amount of MMP-3 at 37° C. for 6 hours. After activation, MMP-3 was completely removed from MMP-1 by affinity chromatography using an anti-MMP-3 IgG Affi-Gel 10 column. The resin, Affi-Gel 10 (Biorad, Emoryville, Calif.), was coupled to anti-MMP-3 IgG (Okada et al., *Annals of Rheumat. Dis.*, 48, 645 (1989)) per the manufacturer's protocol. Pro-MMP-3 was activated by reacting with 5 μg/mL chymotrypsin at 37° C. for 2 hours. Chymotrypsin was inactivated with 2 mM diisopropylfluorophosphate. The amounts of active MMP-1, MMP-2, and MMP-3 were determined by titration with tissue inhibitor of metalloproteinase-1(TIMP1) over a concentration range of 0.1–3 μg/mL, while the amount of active MMP-9 was determined by titration with TIMP-2 (0.1–3 μg/mL). TIMP-1 was isolated from the medium of HT-1080 cells as described in Morodomi et al., *Biochem J.*, 285, 603 (1992).

TIMP-2 was isolated from the conditioned medium of human uterine cervical fibroblasts by applying the medium to a gelatin-Sepharose column (Pharmacia LKB Biotechnology, Piscataway, N.J.). The column is washed with TNC buffer (50 mM Tris-HCl, pH 7.5, 0.15M NaCl, 10 mM $CaCl_2$, 0.02% $NaN_3$) containing 1% dimethylsulfoxide (DMSO). Bound materials are eluted with TNC buffer containing 5% DMSO. The eluted protein peak contains fibronectin, proMMP-2 free from TIMP-2, and proMMP-2-TIMP-2 complexes. To purify TIMP-2 from this mixture, combined peak fractions are concentrated on an Amicon YM-10 membrane (Amicon, Lexington, Mass.) and applied to a Sephacryl S-200 column (Pharmacia LKB Biotechnology, Piscataway, N.J.) equilibrated with 8M urea, 10 mM EDTA, 50 mM Tris-HCl, pH 7.5, 1M NaCl, and $NaN_3$. The fractions containing TIMP-2 are pooled and dialyzed against TNC buffer. The amount of TIMP-2 is measured by titration with a known amount of MMP-3.

Substrates were prepared as 10 mM stock solutions in dimethylsulfoxide (DMSO). Fluorescent assays were performed at $\lambda_{ex}$=325 nm and $\lambda_{em}$=393 nm, which should encounter no interference from Trp residues, using a Hitachi fluorescence spectrophotometer F-3010. Initial total hydrolysis assays were run at a substrate concentration of 5 μM to avoid filtering effects. The change in fluorescence at this concentration was 110 based on total hydrolysis of 1 μM substrate. A typical assay was carried out by incubating 100 μL of various concentrations of a substrate with 10 μL of an enzyme solution (2–20 nM) in 50 mM Tris-HCl, pH 7.5, 0.15M NaCl, 10 mM $CaCl_2$, 0.05% Brij 35, 0.02% $NaN_3$. The reaction was stopped by addition of 900 μl of 3% (v/v) glacial acetic acid. MMP-3 activity at pH 6.0 was measured in 50 mM sodium acetate buffer, pH 6.0, instead of Tris-HCl buffer. The amount of substrate hydrolysis was calculated based on the fluorescence values of the Mca-Arg-Pro-Lys-Pro-Gln standard solution after substraction of the reaction blank value (stopping solution added before the enzyme). Individual kinetic parameters ($k_{cat}$ and $K_M$) were determined over a substrate concentration range of 2.5–75 μM and calculated by double reciprocal plots.

II. DESIGN, SYNTHESIS, AND CHARACTERIZATION OF FLUOROGENIC SUBSTRATES

MMP-3 has a broad substrate specificity which includes extracellular matrix proteins and protease inhibitors (Table 1). In addition, MMP-3 can participate in the activation of proMMP-1, proMMP-3, and proMMP-9 by cleaving specific bonds within the respective propeptides (Table 1). Many MMP-3 substrates contain charged residues in the vicinity of the cleavage site, which would suggest a preference for substrate hydrophilicity that differs from that of MMP-1 (Fields, *J. Theor. Biol.*, 153, 585 (1991)).

TABLE I

Sequences of cleavage sites of MMP-3

| Protein | Sequence[a] | $k_{cat}/K_b$[b] $S^{-1} M^{-1}$ | |
|---|---|---|---|
| Human $\alpha_2$-macroglobulin | Gly—Pro—Glu—Gly$^{679}$—Leu$^{680}$—Arg—Val—Gly | 56,000[c] | Engchild et at., J. Biol. Chem., 264, 8779 1989 |
| | Arg—Val—Gly—Phe$^{684}$—Tyr$^{685}$—Glu—Ser—Asp | | |
| Human $\alpha_1$-antichymotrypain | Leu—Leu—Ser—Ala$^{360}$—Leu$^{361}$—Val—Glu—Thr | 35,000 | Mast et al., J. Biol. Chem., 266, 15810 1991 |
| $\alpha_1$-Protease inhibitor | Glu—Ala—Ile—Pro$^{357}$—Met$^{358}$—Ser—Ile—Pro | 5,400 | Mast et al., 1991 |
| Human aggrecan | Ile—Pro—Glu—Asn$^{341}$—Phe$^{342}$—Phe—Gly—Val | 4,000[d] | Flannery et al., J. Biol. Chem., 267, 1008 1992; Poe et al., Arch. Biochem. Biophys., 298, 75–3, 1992 |
| Substance P | Lys—Pro—Gln—Gln$^6$—Phe$^7$—Phe—Gly—Leu | 1,790 | Teahan et al., Biochem., 28, 8497, 1989 |
| Antithrombin III | Ile—Ala—Gly—Arg$^{385}$—Ser$^{386}$—Leu—Asn—Pro | <50 | Mast et al., 1991 |
| Chicken ovostatin | Leu—Asn—Ala—Gly—Phe—Thr—Ala—Ser | NR[e] (slow) | Engchild et al., 1989 |
| Human pro-MMP-1 | Asp—Val—Ala—Gln$^{80}$—Phe$^{81}$—Val—Leu—Thr | NR | Suzuki et al., Annu. Rev. Cell Biol., 9, 541, 1990 |
| Human pro-MMP-3 | Asp—Thr—Leu—Glu$^{68}$—Val$^{69}$—Met—Arg—Lys | NR | Nagase et al., Biochem., 29, 5783, 1990 |
| Human pro-MMP-3 | Asp—Val—Gly—His$^{82}$—Phe$^{83}$—Arg—Thr—Phe | NR | Nagase et al., 1990 |
| Human pro-MMP-8 | Asp—Ser—Gly—Gly$^{78}$—Phe$^{79}$—Met—Leu—Thr | NR | Knüuper et al., Biochem. J., 295, 581, 1993 |
| Human pro-MMP-9 | Arg—Val—Ala—Glu$^{40}$—Met$^{41}$—Arg—Gly—Glu | NR | Ogata et al., J. Biol. Chem., 267, 3581, 1992 |
| Human pro-MMP-9 | Asp—Leu—Gly—Arg$^{87}$—Phe$^{88}$—Gln—Thr—Phe | NR | Ogata et al., 1992 |
| Bovine $\alpha1$(II) collagen, N-telopeptide | Ala—Gly—Gly—Ala$^{115}$—Gln$^{116}$—Met—Gly—Val | NR | Wu et al., J. Biol. Chem., 266, 5625, 1991 |
| Bovine $\alpha1$(II) collagen, N-telopeptide | Gln—Met—Gly—Val$^{119}$—Met$^{120}$—Gln—Gly—Pro | NR | Wu et al., 1991 |
| Bovine $\alpha1$(IX) collagen, NC2 | —Leu—Lys—Arg—Pro | NR | Wu et al., 1991 |
| Bovine $\alpha2$(IX) collagen, NC2 | —Ala—Lys—Arg—Glu | NR | Wu et al., 1991 |
| Bovine $\alpha3$(IX) collagen, NC2 | —Leu—Arg—Lys—Pro | NR | Wu et al., 1991 |
| Bovine $\alpha1$(XI) collagen, N telopeptide | —Ile—Leu—Gln—Gln | NR | Wu et al., 1991 |
| Human cartilage link | Arg—Ala—Ile—His$^{16}$—Ile$^{17}$—Gln—Ala—Glu | NR | Nguyen et al., Biochem. J., 259, 61, 1989 |
| Bovine fibronectin | Pro—Phe—Ser—Pro$^{689}$—Leu$^{690}$—Val—Ala—Thr | NR | Wilhelm et al., J. Biochem., 268, 21906, 1993 |
| Bovine insulin, B chain | Leu—Val—Glu—Ala$^{14}$—Leu$^{15}$—Tyr—Leu—Val | NR | Azzo and Woessner, J. Biochem., 261, 5434, 1986; Wilhelm et al., 1993 |
| Bovine insulin, B chain | Glu—Ala—Leu—Tyr$^{16}$—Leu$^{17}$—Val—Cys—Gly | NR | Azzo and Woessner, 1986; Wilhelm et al., 1993 |

[a]The $P_1P_1'$ subsites are numbered and/or represented by a "—" between amino acid residues.
[b]Determined at 37° C. unless otherwise noted.
[c]Determined at 25° C..
[d]Determined at 22° C..
[e]NR, not reported.

Substance P is the most directly applicable of the MMP-3 substrates for fluorogenic peptide design, as it is relatively small (11 residues) yet quite susceptible. Initially a substance P sequence with Mca at subsite $P_6$ and Lys(Dnp) at subsite $P_5'$ was prepared. The combination of Mca as fluorophore and Dnp as quencher has several advantages over the more common fluorogenic substrate pair of Trp and Dnp, in that Mca is more fluorescent than Trp and no interference from Trp residues in the MMP is encountered (Knight et al., *FEBS Lett.*, 296, 263 (1992)). Based on these criteria, the initial substrate synthesized was Mca-Pro-Lys-Pro-Gln-Gln-Phe-Phe-Gly-Leu-Lys(Dnp)-Gly (NFF-1). Peptide assembly using Fmoc-Lys(Dnp)-Gly-HMP resin was highly efficient as evaluated by Edman degradation analysis. ESMS analysis of purified NFF-1 gave [M+H]$^+$=1629.8 Da (calculated [M+H]$^+$=1629.6 Da). NFF-1 was hydrolyzed equally well by MMP-3 (FIG. 1A) and MMP-2 (Table 2). MMP-9 and MMP-1 exhibited 60 and 75% less activity, respectively, than MMP-3 towards this substrate primarily due to lower $k_{cat}$ values (Table 2).

TABLE II

Hydrolysis of synthetic substrates by MMPs

| Substrate[a] | Enxyme[b] | $k_{cat}$ $S^{-1}$ | $K_m$ $\mu M$ | $k_{cat}/K_m$ $S^{-1} M^{-1}$ |
|---|---|---|---|---|
| NFF-1 | MMP-1 | 0.04 | 16.6 | 2,510 |
| NFF-1 | MMP-2 | 1.07 | 100 | 10,800 |
| NFF-1 | MMP-3 | 0.53 | 50 | 10,900 |
| NFF-1 | MMP-9 | 0.18 | 45 | 4,000 |
| NFF-2 | MMP-1 | 0.15 | 142 | 1,060 |
| NFF-2 | MMP-2 | 2.70 | 50 | 54,000 |
| NFF-2 | MMP-3 | 3.95 | 66 | 59,400 |
| NFF-2 | MMP-9 | 1.38 | 25 | 55,300 |
| NFF-3 | MMP-1 | ND[c] | ND | ND |
| NFF-3 | MMP-2 | ND | ND | ND |
| NFF-3 | MMP-3 | 5.40 | 25 | 218,000 |
| NFF-3 | MMP-3 (pH 6.0) | 2.20 | 7.5 | 302,000 |

TABLE II-continued

Hydrolysis of synthetic substrates by MMPs

| Substrate[a] | Enxyme[b] | $k_{cat}$ $S^{-1}$ | $K_m$ $\mu M$ | $k_{cat}/K_m$ $S^{-1} M^{-1}$ |
|---|---|---|---|---|
| NFF-3 | MMP-3 (25° C.) | 1.31 | 20 | 65,700 |
| NFF-3 | MMP-9 | 0.282 | 28 | 10,100 |

[a]NFF-1, Mca—Pro—Lys—Pro—Gln—Gln—Phe—Phe—Gly—Leu—Lys (Dnp)—Gly; NFF-2, Mca—Arg—Pro—Lys—Pro—Tyr—Ala—Nva—Trp—Met—Lys(Dnp)—NH$_2$; and NFF-3, Mca—Arg—Pro—Lys—Pro—Val—Glu—Nva—Trp—Arg—Lys(Dnp)—NH$_2$.
[b]Assays were performed at 37° C., pH 7.5, except where noted. Substrates were hydrolyzed exclusively at the Gln—Phe bond for NFF-1, the Ala—Nva bond for NFF-2, and the Glu—Nva bond for NFF-3, with the exception of MMP-1 hydrolysis of NFF-1 occurring at the Gln—Phe and Gly—Leu bonds at a ratio of 3.2, MMP-9 hydrolysis of NFF-1 occurring at the Gly—Leu bond, and MMP-9 hydrolysis of NFF-3 occurring at multiple sites including the Gly—Nva bond. Sites of hydrolysis were determined by Edman degradation analysis after a 36–72 hour treatment of substrate with MMP.
[c]ND, not detectable.

Although the hydrolysis of substance P by MMP-1, MMP-2, or MMP-9 has not been described previously, Gln-Phe bonds have been reported to be hydrolyzed by MMP-1 (Fields, G. B., *The Application of Solid Phase Peptide Synthesis to the Study of Structure Function Relationships in the Collagen-Collagenase System*, Ph.D. Thesis, Florida State University, Tallahassee, Fla., pp. 136–176 (1988)).

The second designed substrate was Mca-Arg-Pro-Lys-Pro-Tyr-Ala-Nva-Trp-Met-Lys(Dnp)-NH$_2$ (NFF-2). Peptide assembly using Fmoc-Lys(Dnp)-DMPAMP resin was highly efficient, and FABMS analysis of purified NFF-2 gave [M+H]$^+$=1641.6 Da (calculated [M+H]$^+$=1640.9 Da). NFF-2 was hydrolyzed 6 times more rapidly than NFF-1 by MMP-3 (FIG. 1B), which was mostly due to an increase in $k_{cat}$ (Table 2). MMP-1 activity toward NFF-2 was reduced by ~50% compared to NFF-1 largely due to an increase in $K_M$ (Table 2). The two concommittal changes that most likely effected MMP-1 hydrolysis were the elimination of the second cleavage site in NFF-1 (the Gly-Leu bond) and replacement of Gly by Met in subsite P$_3$' (Fields, *The Application of Solid Phase Peptide Synthesis to the Study of Structure Function Relationships in the Collagen-Collagenase System*, Ph.D. Thesis, Florida State University, Tallahassee, Fla., pp. 136–176 (1988)). Unfortunately, NFF-2 was hydrolyzed 5 and 14 times more rapidly than NFF-1 by MMP-2 and MMP-9, respectively (Table 2). KM had decreased and kca had increased for both MMP-2 and MMP-9 (Table 2). NFF-2 is the most rapidly hydrolyzed substrate for MMP-9 reported to date.

Figure 2:
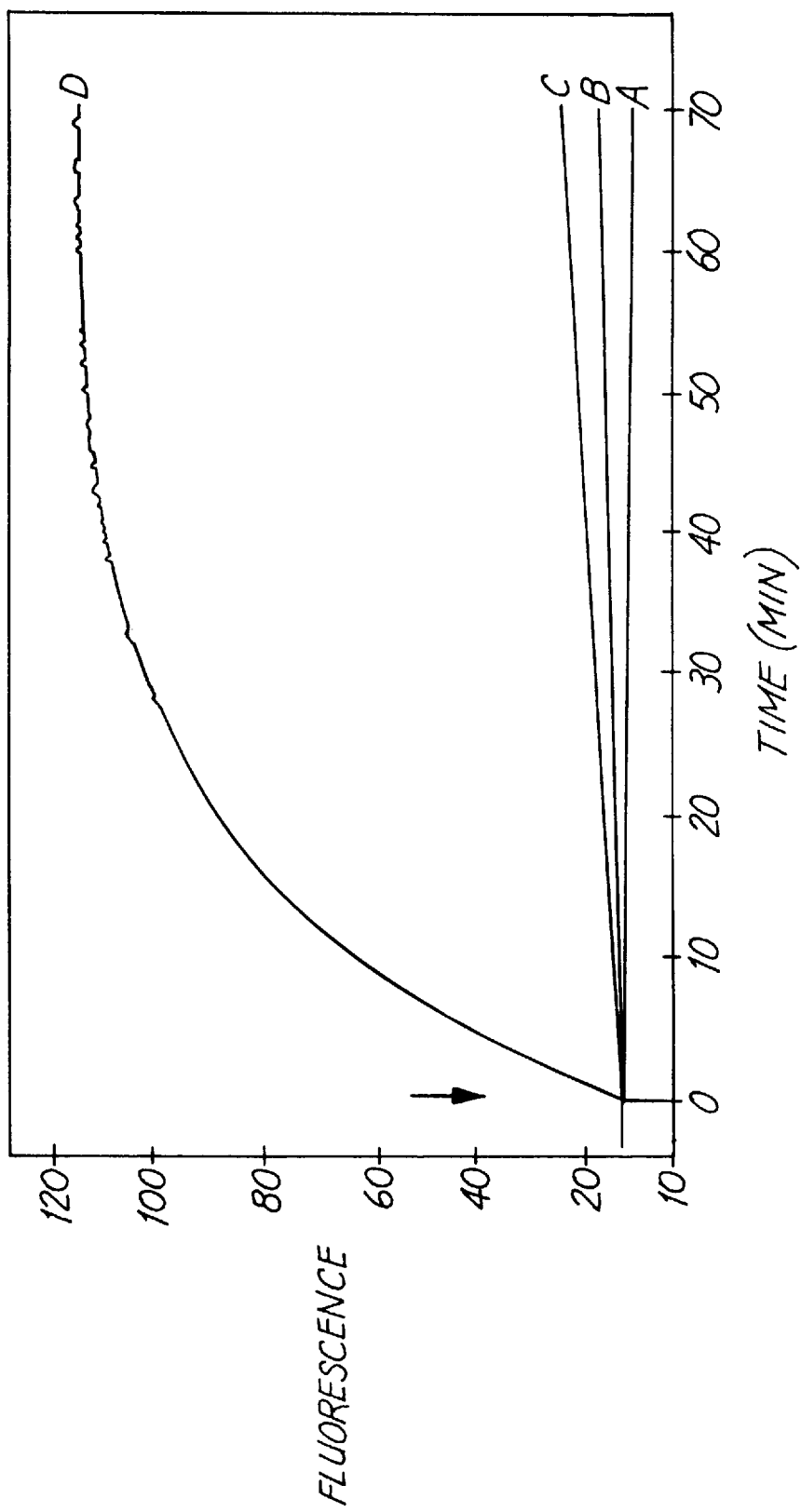
FIG. 2 Continuous fluorometric assay of NFF-3 [Mca-Arg-Pro-Lys-Pro-Val-Glu-Nva-Trp-Arg-Lys(Dnp)-NH$_2$] with (a) MMP-1, (b) MMP-2, (c) MMP-9, and (d) MMP-3. Assays were performed at 37° C., pH 7.5, by reacting 1 $\mu$M substrate and 200 ng of each MMP in a 1 mL solution. Fluorescence was read with $\lambda_{ex}$=325 nm and $\lambda_{em}$=393 nm.

Although NFF-2 was hydrolyzed 60 times more rapidly by MMP-3 than MMP-1, comparison of protein substrates and sequence specificity studies indicated that a few substitutions could provide even greater discrimination between MMP-3 and MMP-1 while possibly reducing MMP-2 and MMP-9 activities. In particular, charged residues in subsite P$_1$ are better tolerated by MMP-3 than MMP-1. NFF-2 was modified by replacing Tyr with Val in subsite P$_2$, Ala with Glu in subsite P$_1$, and Met with Arg in subsite P$_3$', resulting in Mca-Arg-Pro-Lys-Pro-Val-Glu-Nva-Trp-Arg-Lys(Dnp)-NH$_2$ (NFF-3). FABMS analysis of purified NFF-3 gave [M+H]$^+$=1660.9 Da (calculated [M+H]$^+$=1659.9 Da). NFF-3 was hydrolyzed 3.7 times faster than NFF-2 by MMP-3 (FIG. 1C; Table 2) due to both a decrease in $K_M$ and an increase in $k_{cat}$. NFF-3 was not hydrolyzed by either MMP-1 (FIG. 2D) or MMP-2 (FIG. 2C) and very slowly hydrolyzed by MMP-9 (FIG. 2B; Table 2). For MMP-9, the $k_{cat}$, value had decreased (Table 2).

III. DISCUSSION

NFF-3 is the first synthetic substrate that has been shown to have discriminatory activities for members of the MMP family. The cleavage site in NFF-3 (Glu-Nva) is very similar sterically to the initial MMP-3 cleavage site in proMMP-9 (a Glu-Met bond; Table 1). MMP-1, MMP-2, and MMP-9 do not cleave this bond (Ogata et al., *J. Biol. Chem.*, 267, 3581 (1992)). A comparison of synthetic substrates (Table 3) indicates that NFF-3 is also the most rapidly hydrolyzed fluorogenic MMP-3 substrate yet described. Although the rate of MMP-3 hydrolysis of NFF-3 is just slightly better than that of Dnp-Arg-Pro-Lys-Pro-Leu-Ala-Nva-Trp-NH$_2$ (Niedzwiecki et al., *Biochem.*, 31, 12618 (1992)), NFF-3 has the advantage of not requiring a Trp residue for fluorescence and thus is not subject to interference from the MMP itself. In addition, Dnp-Arg-Pro-Lys-Pro-Leu-Ala-Nva-Trp-NH$_2$ is most likely hydrolyzed by other MMPs based on our results for NFF-2. NFF-3 is soluble up to a concentration of 250 $\mu$M using 2.5% DMSO in water, which appears to be better than the solubility of the previously described Mca-peptide substrate for MMP-3 (Knight et al., *FEBS Lett.*, 296, 263 (1992)). The detection sensitivity of NFF-3, due to the highly fluorescent Mca group, allows for the use of this substrate under first order conditions, i.e., at a concentration well below the MMP-3 $K_M$ value of 25 $\mu$M.

TABLE III

Fluorogenic Stromelysin Substrate
Hydrolysis of synthetic substrates by MMP-3

| Substrate[a] | $k_{cat}$[b] $S^{-1}$ | $K_m$[b] $\mu M$ | $k_{cat}K_m$[b] $S^{-1} M^{-1}$ | Ref. |
|---|---|---|---|---|
| Gly—Pro—Gln—Gly"—"Ile—Ala—Met—Gln | 0.69[c] | 5600[c] | 120[c] | Fields, 1988 |
| Dnp—Pro—Leu—Gly"—"Leu—Trp—Ala—D—Arg—NH$_2$ | NR[d] | NR | 2,200 | Knight et al., 1992 |
| Dnp—Pro—Tyr—Ala"—"Tyr—Trp—Met—Arg—NH$_3$ | 0.24[e] | 100[c] | 2,400 | Netzel-Arnett et al., J. Biol. Chem., 266, 6747; J. Biol. Chem., 266, 21326, 1991 |
| Mca—Pro—Lys—Pro—Gln—Gln"—"Phe—Phe—Gly—Gly—Leu—Lys—(Dnp)—Gly | 0.53 | 50 | 10,900 | This study |
| Mca—Pro—Leu—Gly"—"Leu—Dpa—Ala—Arg—NH$_2$ | NR | NR | 23,000 | Knight et al., 1992 |
| Mca—Arg—Pro—Lys—Pro—Tyr—Ala"—"Nva—Trp—Met—Lys—(Dnp)—NH$_2$ | 3.95 | 66 | 59,400 | This study |
| Dnp—Arg—Pro—Lys—Pro—Leu—Ala"—"Nva—Trp—NH$_2$ | NR | NR | 45,000[f] | Niedzwiccki et al., Biochem., 31, 12618, 1992 |

TABLE III-continued

Fluorogenic Stromelysin Substrate
Hydrolysis of synthetic substrates by MMP-3

| Substrate[a] | $k_{cat}^{b}$ $S^{-1}$ | $K_m^{b}$ $\mu M$ | $k_{cat}K_m^{b}$ $S^{-1} M^{-1}$ | Ref. |
|---|---|---|---|---|
| Mca—Arg—Pro—Lys—Pro—Val—Glu"—"Nva—Trp—Arg—Lys(Dnp)—NH$_2$ | 1.31[f] | 20[f] | 65,700[f] | This study |
| Mca—Arg—Pro—Lys—Pro—Val—Glu"—"Nva—Trp—Arg—Lys(Dnp)—NH$_2$ | 5.40 | 25 | 218,000 | This study |

[a]Sites of hydrolysis are indicated by "—" between amino acid residues.
[b]Assays were performed at 37° C. except where noted.
[c]Assay performed at 30° C..
[d]NR, not reported.
[e]Assay performed at 23° C..
[f]Assay performed at 25° C..

The complete disclosure of all patents, patent documents, and publications cited herein are incorporated by reference, as if individually incorporated. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A peptide compound of the formula Mca-Arg-Pro-Lys-Pro-Tyr-Ala-Nva-Trp-Met-Lys(Dnp)-NH$_2$.

2. A peptide compound of the formula Mca-Arg-Pro-Lys-Pro-Val-Glu-Nva-Trp-Arg-Lys(Dnp)-NH$_2$.

* * * * *

UNITED STATES PATENT AND TRADEMARK OFFICE
CERTIFICATE OF CORRECTION

PATENT NO. : 5,770,691
DATED : June 23, 1998
INVENTOR(S) : Gregg B. Fields and Hideaki Nagase It is certified that error appears in the above-identified patent and that said Letters Patent is hereby corrected as shown below:

Col. 3, line 62, delete "(B) McaArg" and insert --(B) Mca-Arg--;
Col. 3, line 63, delete "(C) McaArg" and insert --(C) Mca-Arg--;
Col. 3, line 64, delete "NH2" and insert -- $NH_2$--;
Col. 4, lines 14-15, delete "mechanism (s)" and insert --mechanism(s)--;
Col. 6, line 40, delete "Fmoc-Lvs(Dnp)" and insert --Fmoc-Lys(Dnp)--;
Col. 6, line 62, delete "FmocLys(Dnp)" and insert --Fmoc-Lys(Dnp)--;
Col. 8, line 13, delete "(TIMP1)" and insert --(TIMP-1)--;
Col. 9-10, Table I, 3rd column heading, delete "$k_{cat}/K_b^b$" and insert --$k_{cat}/K_m^b$--;
Col. 9-10, Table I, footnotes, delete "$^a$The $P_1P_1^5$" and insert --$^a$The $P_1P_1'$--;
Col. 11, line 47, delete "KM" and insert --$K_M$--;

UNITED STATES PATENT AND TRADEMARK OFFICE
CERTIFICATE OF CORRECTION

PATENT NO. : 5,770,691
DATED : June 23, 1998
INVENTOR(S) : Gregg B. Fields and Hideaki Nagase It is certified that error appears in the above-identified patent and that said Letters Patent is hereby corrected as shown below:

Col. 11, line 48, delete "kca" and insert --$k_{cat}$--;

Col. 12, line 21, delete "$k_{cat}$," and insert --$k_{cat}$--; and

Col. 11-12, Table III, 4th line under heading "Substrate", delete "Mca-Pro-Lys-Pro-Gln-Gln"-"Phe-Phe-Gly-Gly-Leu-Lys-(Dnp)-Gly" and insert --Mca-Pro-Lys-Pro-Gln-Gln"-"Phe-Phe-Gly-Leu-Lys-(Dnp)-Gly--.

Signed and Sealed this

Fourth Day of May, 1999

Attest:

Q. TODD DICKINSON

*Attesting Officer*          *Acting Commissioner of Patents and Trademarks*